United States Patent [19]

Grenacher et al.

[11] Patent Number: 4,709,105
[45] Date of Patent: Nov. 24, 1987

[54] PREPARATION OF $C_3$-$C_{25}$-ALKANOLS

[75] Inventors: Armin V. Grenacher, Mutterstadt; Max Strohmeyer, Limburgerhof; Herwig Hoffmann, Frankenthal; Heinrich Elliehausen, Ludwigshafen, all of Fed. Rep. of Germany

[73] Assignee: BASF Aktiengesellschaft, Ludwigshafen, Fed. Rep. of Germany

[21] Appl. No.: 932,637

[22] Filed: Nov. 19, 1986

[30] Foreign Application Priority Data

Dec. 3, 1985 [DE] Fed. Rep. of Germany ....... 3542595

[51] Int. Cl.$^4$ ..................... C07C 29/14; C07C 31/125
[52] U.S. Cl. .................................. 568/883; 568/881
[58] Field of Search .............................. 568/883, 881

[56] References Cited

U.S. PATENT DOCUMENTS

| | | | |
|---|---|---|---|
| 3,118,954 | 1/1964 | Robbins et al. | 568/883 |
| 3,288,866 | 11/1966 | Cooper | 568/881 |
| 3,431,311 | 3/1969 | Cooper et al. | 568/881 |
| 3,491,158 | 1/1970 | Reich | 568/881 |
| 3,491,159 | 1/1970 | Reich et al. | 568/881 |
| 3,880,940 | 4/1975 | Baer et al. | 568/881 |
| 4,021,497 | 5/1977 | Adam et al. | 568/881 |
| 4,426,541 | 1/1984 | King | 568/883 |

FOREIGN PATENT DOCUMENTS 2257673 3/1974 Fed. Rep. of Germany.
2321101 11/1974 Fed. Rep. of Germany.

*Primary Examiner*—J. E. Evans
*Attorney, Agent, or Firm*—John H. Shurtleff

[57] ABSTRACT

Preparation of $C_3$- to $C_{25}$-alkanols by catalytic hydrogenation of corresponding crude $C_3$- to $C_{25}$-alkanols, as obtained in the cobalt-catalyzed hydroformylation of $C_2$- to $C_{24}$-olefins, by partial 80–95% hydrogenation conversion in a first stage using a silica supported nickel and molybdenum oxide catalyst and then completing the conversion in a second stage using a cobalt catalyst containing copper, manganese, molybdenum and, optionally other activating additives. The process is especially adapted to the economic preparation of $C_9$–$C_{11}$- and $C_{13}$–$C_{15}$-alkanols which are used to prepare high-grade plasticizer esters.

5 Claims, No Drawings

PREPARATION OF $C_3$-$C_{25}$-ALKANOLS

The present invention relates to an improved process for the preparation of $C_3$-$C_{25}$-alkanols by catalytic hydrogenation of the corresponding crude alkanals, as obtained in the cobalt-catalyzed hydroformylation of $C_2$-$C_{24}$-olefins.

It is well known that alkanals can be hydrogenated with hydrogen, using a nickel-containing supported catalyst, to give the corresponding alkanols. Where pure aldehydes are involved, this hydrogenation does not present any problems; however, the hydrogenation entails considerable technical difficulties in the case of crude alkanals, as obtained in the cobalt-catalyzed hydroformylation of the corresponding olefins, since the crude alkanals still contain various byproducts, which also have to be hydrogenated, either because, as in the case of formates and acetals, they likewise have to be converted to the desired alkanol

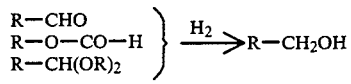

R = Alkyl so that no alkanol is lost, or because the byproducts, if they were not hydrogenated or were incompletely hydrogenated, would result in a considerable deterioration in the quality of the alkanols.

Since the hydrogenation of the byproducts takes place more slowly than that of the alkanals under otherwise identical conditions, and consequently the space-time yields for complete conversion are uneconomically low, it is necessary, in order to overcome this disadvantage, to make the reaction conditions more severe and carry out the reaction at a higher temperature, under higher pressure, with a more active catalyst and/or with a larger amount of catalyst. However, this would lead to new problems since firstly there is a danger that the (exothermic) hydrogenation would go out of control and secondly the undesirable Fischer-Tropsch reaction, i.e. the formation of paraffins from the carbon monoxide originating from the hydrogenation of formate, would be favored, the lower paraffins having an adverse effect on the quality of the alkanol, and the higher ones remaining on the catalyst and deactivating it prematurely.

It is also well known that cobalt catalysts can be used for the hydrogenation of alkanals. In general, these have the advantage that, in the case of the crude alkanals, the byproducts are also hydrogenated without the above complications being encountered: however, cobalt catalysts are substantially more expensive than nickel ones. Moreover, they have a shorter life, which becomes all the shorter the higher the operating temperatures; however, it is precisely higher temperatures which are necessary for achieving complete conversion, unless long reaction times are acceptable.

It is an object of the present invention to avoid the disadvantages described in the hydrogenation of crude alkanals and to design the hydrogenation process to be overall more economical than hitherto.

We have found that this object is achieved by an improved process for the preparation of $C_3$-$C_{25}$-alkanols by catalytic hydrogenation of the corresponding crude alkanals, as obtained in the cobalt-catalyzed hydroformylation of $C_2$-$C_{24}$-olefins, wherein (a) the hydrogenation is carried out in a first stage to a hydrogen conversion of 80–95% at 150°–230° C. and under 10–350 bar using an $SiO_2$ supported catalyst which contains 5–15% by weight of nickel and 2–20% by weight of molybdenum in the form of molybdenum oxide, the percentages in each case being based on the total weight of the catalyst including the support, and (b) the hydrogenation is completed in a second stage at 150°–230° C. and under 10–350 bar with the aid of a cobalt catalyst whose active material consists of 55–65% by weight of cobalt,
15–20% by weight of copper,
4–10% by weight of manganese,
2–5% by weight of molybdenum in the form of molybdenum oxide and
0–10% by weight of other activating additives.

A large number of the nickel/molybdenum catalysts conforming to the definition are known per se. They are advantageously prepared by impregnating silica carriers with an aqueous solution of a nickel or molybdenum salt, molding the material and then drying and, if necessary, heating it. Examples of suitable nickel salts for this purpose are the nitrate, the chloride, the formate and the acetate, the sulfate being less suitable because it is reduced to the sulfide under the hydrogenation conditions, and the sulfide may deactivate the catalyst. The most suitable molybdenum salt is ammonium molybdate. In addition to the nickel and molybdenum, these catalysts may also contain activating components, such as copper and/or magnesium, these metals being applied to the carrier similarly to the nickel and molybdenum. The ratios of the stated components depend on the corresponding amounts in the prepared, reduced catalyst.

The prepared catalysts are then advantageously heated at about 300°–500° C. under hydrogen atmosphere, the nickel and other reducible components being converted to the active metallic form. However, this pretreatment is not absolutely essential since the active form of the catalysts is also formed under the conditions of aldehyde hydrogenation.

Suitable catalysts of this type and their preparation are described in German Patent No. 2,257.673. They consist of, for example, 5–15% by weight of Ni and 5–20% by weight of Mo in the form of $MoO_3$, the remainder being a heat-treated $SiO_2$ carrier.

The cobalt catalysts conforming to the definition, and their preparation, are likewise known per se, in particular from German Laid-Open Application DOS No. 2,321,101, which may be referred to in connection with the preparative details.

In both stages of the novel process, the catalyst is advantageously used as the fixed-bed catalyst in a pressure-resistant reactor or in a plurality of tubes (tube-bundle reactor). The amounts required correspond to a space velocity of about 0.5–1.5 kg of crude alkanal per L of catalyst per hour in the case of the nickel/molybdenum catalsts, and about 1.0–3.0 kg of crude alkanal per L of catalyst per hour in the case of the cobalt catalysts.

The first hydrogenation stage is preferably carried out at 160°–220° C. and under an $H_2$ pressure of 20–280 bar, while temperatures of from 155 to 210° C. and an $H_2$ pressure of 20–280 bar are particularly preferred for the second stage.

Under these conditions, the hydrogenation in the first stage takes about 0.5–1.5 hours at a conversion of 80–95%, about 20–40 minutes being required for the remaining conversion in the second stage.

These values give space-time yields of about 0.4–1.0 kg $L^{-1}h^{-1}$. Although such advantageous values can also be obtained when the cobalt catalysts conforming to the definition are used alone, they can be achieved only with substantially lower cost-effectiveness, since firstly the cobalt catalysts are substantially more expensive and secondly they possess a considerably shorter life, the comparison in each case being made with the nickel/molybdenum catalysts.

The novel process is useful for the hydrogenation of any crude alkanals which are obtained from the cobalt-catalyzed hydroformylation of $C_2$–$C_{24}$-olefins, i.e. which, in addition to the n- and iso-alkanals, also contain acetals and formates as the principal byproducts. The process is particularly important for the preparation of higher primary alkanols from δ-olefins, such as $C_9$–$C_{11}$-and $C_{13}$–$C_{15}$-alkanols, since these alkanols are used for the preparation of high-grade plasticizer esters which have to meet extremely high quality requirements with regard to color, odor and performance characteristics.

EXAMPLE 3.2 kg of a crude $C_9$–$C_{11}$-alkanal which has been obtained by cobalt-catalyzed hydroformylation of a $C_8$–$C_{10}$-olefin mixture and contained, inter alia, 6% by weight of $C_9$–$C_{11}$-alkyl formates and 7% by weight of acetals as byproducts, were passed over 4.3 L of a nickel/molybdenum catalyst at 170° C. and under an $H_2$ pressure of 250 bar, the mean contact time being about 1 hour. This hydrogenation was carried out to a conversion of 95%.

In a second hydrogenation stage, conversion was completed at 170° C. and under 245 bar over 2.2 l of cobalt catalyst during a mean contact time of 0.5 hour.

The yield of a corresponding alkanol was 99.6%, based on the amount theoretically obtainable from the stated crude product. This yield corresponded to a spacetime yield of 0.5 kg $l^{-1}h^{-1}$.

In the reduced form, the nickel/molybdenum catalyst prepared by the method of Example 1 of German Patent No. 2,257,673 consisted of 81.7% by weight of $SiO_2$, 8.3% of Ni and 10.0% by weight of Mo (as $MoO_3$). It was in the form of extrudates having a diameter of 6 mm and a length of 15–30 mm.

The cobalt catalyst was prepared by the method of Example 1 of German Laid-Open Application DOS No. 2,321,101. In the reduced form, it was composed of 59.1% by weight of Co, 17.2% by weight of Cu, 5.8% by weight of Mn (as the oxide), 2.7% by weight of Mo (as the oxide) and 3.2% by weight of phosphoric acid, the remainder being oxidic oxygen. The extrudates had a diameter of 4 mm and a length of 7–15 mm.

When the nickel catalyst was used alone, it was only possible to achieve a space-time yield of 0.37 kg $l^{-1}h^{-1}$.

We claim:

1. In a process for the preparation of a $C_3$–$C_{25}$-alkanol by catalytic hydrogenation of the corresponding crude alkanal, as obtained in the cobalt-catalyzed hydroformylation $C_2$–$C_{24}$-olefins, the improvement comprising:
   (a) carrying out the hydrogenation in a first stage to a hydrogen conversion of 80–95% at 150°–230° C. and under 10–350 bar using an $SiO_2$ supported catalyst which contains 5–15% by weight of nickel and 2–20% by weight of molybdenum in the form of molybdenum oxide, the percentages in each case being based on the total weight of catalyst including support; and
   (b) completing the hydrogenation in a second stage at 150°–230° C. and under 10–350 bar with the aid of a cobalt catalyst whose active material consists of
   55–65% by weight of cobalt,
   15–20% by weight of copper,
   4–10% by weight of manganese,
   2–5% by weight of molybdenum in the form of molybdenum oxide, and
   0–10% by weight of other activating additives.

2. A process as claimed in claim 1 wherein the first stage hydrogenation is carried out at 160°–220° C. and under a hydrogen pressure of 20–280 bar and the second stage hydrogenation is carried out at 155° C. and under a hydrogen pressure of 20–280 bar.

3. A process as claimed in claim 2 wherein the first stage hydrogenation is carried out over a reaction time of about 0.5–1.5 hours, and the second stage hydrogenation is carried out over a reaction time of about 20–40 minutes.

4. A process as claimed in claim 1 wherein the initial reactant is a crude mixture of $C_9$–$C_{11}$-alkanals.

5. A process as claimed in claim 1 wherein the initial reactant is a crude mixture of $C_{13}$–$C_{15}$-alkanals.

* * * * *